United States Patent
Nagayoshi et al.

(10) Patent No.: US 11,457,838 B2
(45) Date of Patent: Oct. 4, 2022

(54) TARGET MANAGEMENT SYSTEM AND TRANSITORY RECORDING MEDIUM COMPRISING TARGET MANAGEMENT PROGRAM

(71) Applicants: OMRON HEALTHCARE Co., Ltd., Kyoto (JP); OMRON Corporation, Kyoto (JP)

(72) Inventors: Sho Nagayoshi, Kyoto (JP); Hiroshi Koshimizu, Kyoto (JP); Ken Miyagawa, Kyoto (JP); Keiichi Obayashi, Kyoto (JP)

(73) Assignees: OMRON HEALTHCARE CO., LTD., Muko (JP); OMRON CORPORATION, Kyoto (JP)

( * ) Notice: Subject to any disclaimer, the term of this patent is extended or adjusted under 35 U.S.C. 154(b) by 364 days.

(21) Appl. No.: 16/851,255

(22) Filed: Apr. 17, 2020

(65) Prior Publication Data
US 2020/0237263 A1    Jul. 30, 2020

Related U.S. Application Data

(63) Continuation of application No. PCT/JP2018/039019, filed on Oct. 19, 2018.

(30) Foreign Application Priority Data

Oct. 26, 2017  (JP) .............................. JP2017-207223
Oct. 26, 2017  (JP) .............................. JP2017-207224

(51) Int. Cl.
*A61B 5/00*     (2006.01)
*A61B 5/11*     (2006.01)
*G09B 19/00*    (2006.01)

(52) U.S. Cl.
CPC .......... *A61B 5/1118* (2013.01); *A61B 5/0022* (2013.01); *A61B 5/1112* (2013.01); *G09B 19/003* (2013.01)

(58) Field of Classification Search
CPC ... A61B 5/1118; A61B 5/0022; A61B 5/1112; G09B 19/003; G16H 20/30; G16H 20/60; G16H 20/70
See application file for complete search history.

(56) References Cited

U.S. PATENT DOCUMENTS

2007/0168230 A1*  7/2007  Roman ................. G16H 20/30
                                                                  482/8
2010/0235181 A1*  9/2010  Loser .................... G16H 50/20
                                                                  705/2
(Continued)

FOREIGN PATENT DOCUMENTS

JP      2013-109718 A    6/2013
JP      2014048923 A     3/2014
(Continued)

OTHER PUBLICATIONS

International Search Report of the International Searching Authority for PCT/JP2018/039019 dated Dec. 12, 2018.
(Continued)

*Primary Examiner* — Ojiako K Nwugo
(74) *Attorney, Agent, or Firm* — Birch, Stewart, Kolasch & Birch, LLP

(57) ABSTRACT

Whether intervention is necessary is assessed due to an occurrence of a divergence of a current value of a predetermined index from a route corresponding to a transition in value of the predetermined index to a target value of the predetermined index for reaching a target relating to a body of a user (steps S141 to S147), and, when intervention is assessed to be necessary, using an intervention result per each of persons intervening relating to a target index stored
(Continued)

in a storage unit, a person with a high contribution toward reaching the target from among persons intervening for the user is determined (steps S151 and S152), and processing for prompting the determined person for intervention is executed (step S155). A timing with a high contribution is determined using an intervention result stored in the storage unit that further stores intervention results per each intervention timing relating to a target index. Processing for prompting the person intervening for intervention at the determined timing is executed. This can effectively prompt the user to improve to reach a target relating to the body.

10 Claims, 24 Drawing Sheets

(56) References Cited

U.S. PATENT DOCUMENTS

| | | | | |
|---|---|---|---|---|
| 2011/0054867 | A1* | 3/2011 | Firminger | G06Q 10/10 |
| | | | | 709/204 |
| 2013/0216982 | A1* | 8/2013 | Bennett | A61B 5/4866 |
| | | | | 434/127 |
| 2014/0285491 | A1 | 9/2014 | Otsubo et al. | |
| 2014/0366878 | A1* | 12/2014 | Baron | G16H 40/60 |
| | | | | 128/204.23 |
| 2015/0133743 | A1* | 5/2015 | Baron | G16H 30/40 |
| | | | | 600/512 |
| 2015/0342511 | A1* | 12/2015 | Goldberg | G09B 19/00 |
| | | | | 434/236 |
| 2016/0317074 | A1 | 11/2016 | Kawai et al. | |
| 2016/0317099 | A1 | 11/2016 | Kawai et al. | |
| 2016/0328524 | A1 | 11/2016 | Kawai et al. | |
| 2016/0328533 | A1 | 11/2016 | Kawai et al. | |
| 2016/0328534 | A1 | 11/2016 | Kawai et al. | |
| 2016/0335401 | A1 | 11/2016 | Kawai et al. | |
| 2016/0335402 | A1 | 11/2016 | Kawai et al. | |
| 2017/0135495 | A1 | 5/2017 | Hattori | |
| 2017/0136348 | A1 | 5/2017 | Hattori et al. | |
| 2019/0221303 | A1* | 7/2019 | Bennett | G16H 10/20 |

FOREIGN PATENT DOCUMENTS

| | | | |
|---|---|---|---|
| JP | 2016085703 | A | 5/2016 |
| JP | 2016189059 | A | 11/2016 |
| JP | 2017117379 | A | 6/2017 |
| WO | WO 2015/107744 | A1 | 7/2015 |
| WO | WO2015107748 | A1 | 7/2015 |

OTHER PUBLICATIONS

Translation of the International Search Report of the International Searching Authority for PCT/JP2018/039019 dated Dec. 18, 2018.

* cited by examiner

GROUP PERFORMANCE OF INTERVENTION EFFECTIVENESS

| USER | SET TARGET INDEX | ... | EFFECTIVE INTERVENTION METHOD | FINAL TARGET ACHIEVEMENT |
|---|---|---|---|---|
| USER A | MUSCLE MASS | ... | SMART PHONE NOTIFICATION | ○ |
| USER B | WEIGHT | ... | WORDS AND ACTIONS BY WIFE | × |
| USER C | BLOOD PRESSURE | ... | WORDS AND ACTIONS BY PHYSICIAN | × |
| USER D | BLOOD PRESSURE | ... | WORDS AND ACTIONS BY HEALTH PROFESSIONAL | ○ |
| USER E | MUSCLE MASS | ... | WORDS AND ACTIONS BY WIFE | ○ |
| USER F | MUSCLE MASS | ... | WORDS AND ACTIONS BY WIFE | × |
| ... | ... | ... | ... | ... |

FIG. 16

| USER | SET TARGET INDEX | ... | EFFECTIVE INTERVENTION METHOD | FINAL TARGET ACHIEVEMENT |
|---|---|---|---|---|
| USER A | MUSCLE MASS | ... | SMART PHONE NOTIFICATION | ○ |
| USER B | WEIGHT | ... | WORDS AND ACTIONS BY WIFE | × |
| USER C | BLOOD PRESSURE | ... | WORDS AND ACTIONS BY PHYSICIAN | × |
| USER D | BLOOD PRESSURE | ... | WORDS AND ACTIONS BY HEALTH PROFESSIONAL | ○ |
| USER E | MUSCLE MASS | ... | WORDS AND ACTIONS BY WIFE | ○ |
| USER F | MUSCLE MASS | ... | WORDS AND ACTIONS BY WIFE | × |
| ... | ... | ... | ... | ... |

FIG. 18

PERFORMANCE OF INTERVENTION EFFECTIVENESS FOR INDIVIDUAL (EXAMPLE: USER B)

| INTERVENTION TIME | INTERVENTION METHOD | PRESENCE OF INTERVENTION EFFECT |
|---|---|---|
| 2017/5/26 | SMART PHONE NOTIFICATION | × |
| 2017/5/26 | WORDS AND ACTIONS BY WIFE | ○ |
| 2017/5/27 | WORDS AND ACTIONS BY WIFE | ○ |
| 2017/5/29 | WORDS AND ACTIONS BY COMPANY SUPERVISOR | ○ |
| 2017/5/30 | WORDS AND ACTIONS BY WIFE | × |
| 2017/5/31 | WORDS AND ACTIONS BY PHYSICIAN | × |
| ... | ... | ... |

FIG. 20

| MEASUREMENT TIME | WEIGHT [ kg ] |
|---|---|
| 2017/5/26 | 65.25 |
| 2017/5/26 | 65.50 |
| 2017/5/27 | 67.00 |
| 2017/5/29 | 68.00 |
| 2017/5/30 | 66.00 |
| 2017/5/31 | 65.25 |
| ... | ... |

FIG. 22

TARGET MANAGEMENT SYSTEM AND TRANSITORY RECORDING MEDIUM COMPRISING TARGET MANAGEMENT PROGRAM

CROSS-REFERENCE TO RELATED APPLICATIONS

This is a continuation of International Application 2017-207223, with an international filing date of Oct. 26, 2017, International Application 2017-207224 with an international filing date of Oct. 26, 2017 and International Application PCT/JP2018/039019, with an international filing date of Oct. 19, 2018, filed by applicant, the disclosure of which is hereby incorporated by reference in its entirety.

TECHNICAL FIELD

This disclosure relates to a target management system and a transitory recording medium comprising a target management program. In particular, this disclosure relates to a target management system and a transitory recording medium comprising target management program appropriate for managing a target relating to the body of a user.

BACKGROUND ART

Systems for managing a target relating to the body of a user are known. In such systems, to increase the quality of life (QOL) of the user in terms of health, for example, a server sends advisory information to the family as a notification target. The family then notified the user of the advisory information at an appropriate timing (for example, see WO 2015/107744 (hereinafter referred to as "Patent Document 1").

CITATION LIST

Patent Literature

Patent Document 1: WO 2015/107744
Patent Document 2: JP 2013-109718 A

SUMMARY OF INVENTION

Technical Problem

However, the system of Patent Document 1 does not take into consideration how to select a family that notifies the user of the advisory information. Thus, the user may not be effectively prompted to improve to reach a target relating to the body.

An object of an aspect of this disclosure is to provide a target management system and a target management program that are capable of effectively prompting a user to improve to reach a target relating to the body.

Solution to Problem

A target management system according to an aspect of the disclosure includes an assessment unit, a storage unit, a determination unit, and an execution unit. The assessment unit is configured to assess whether intervention is necessary due to an occurrence of a divergence of the current value of a predetermined index from a route corresponding to a transition in value of a predetermined index to a target value of a predetermined index for reaching a target relating to the body of the user. The storage unit is configured to store an intervention result per each of persons intervening relating to a target index. The determination unit is configured to determine, when the assessment unit assesses that intervention is necessary, a person with high contribution toward reaching the target, from among the persons intervening for the user, using the intervention result stored in the storage unit. The execution unit is configured to execute processing for prompting the person determined by the determination unit for intervention.

Preferably, the storage unit is configured to further store an intervention result per each timing of intervention relating to a target index. The determination unit is configured to determine a timing with a high contribution toward reaching the target using an intervention result stored in the storage unit. The execution unit is configured to execute processing for prompting the person intervening, for intervention to intervene at the timing determined by the determination unit.

Preferably, the determination unit is configured to determine a person with high contribution corresponding to a habit of the user for each day.

Preferably, a calculation unit is further provided which is configured to calculate a degree of divergence of the current value of the predetermined index from the route. The determination unit is configured to determine an intervention method corresponding to the degree of divergence. The execution unit is configured to execute processing for intervention for the user by the intervention method.

Preferably, the determination unit is configured to determine a person intervening for the user as the intervention method. The execution unit is configured to execute processing for prompting the person determined by the determination unit for intervention as processing for intervention for the user.

Preferably, a storage unit is further provided which is configured to store in advance determining information for determining a statistically effective intervention method, and the determination unit is configured to determine a statistically effective intervention method for the user using the determining information stored in the storage unit. More preferably, the storage unit is configured to associate and store in advance a target relating to a body of each of a plurality of persons and an effective intervention method as the determining information, and the determination unit is configured to determine an intervention method on the basis of an intervention method for a person with a similar target to the user from among the intervention methods stored in the storage unit. More preferably, the storage unit is configured to store in advance an intervention method that was previously effective for the user as the determining information, and the determination unit is configured to determine an intervention method on the basis of the intervention method stored in the storage unit.

A target management program according to yet another aspect of the disclosure is executed by a server including a storage unit configured to store an intervention result per each of persons intervening relating to a target index relating to a body of a user. The target management program includes the steps executed by the server of assessing whether intervention is necessary due to an occurrence of a divergence of a current value of a predetermined index from a route corresponding to a transition in value of the predetermined index to a target value of the predetermined index for reaching a target relating to a body of a user, determining, when assessed that intervention is necessary, a person with a high contribution toward reaching the target, from among the persons intervening for the user, using the intervention result stored in the storage unit, and executing processing for prompting a person determined for intervention.

Preferably, the server further executes the steps of calculating a degree of divergence of the current value of the predetermined index from the route, determining an intervention method corresponding to the degree of divergence calculated, and executing processing for intervention for the user by the intervention method determined.

Advantageous Effects of Invention

An aspect of this disclosure can provide a target management system and a transitory recording medium comprising a target management program that are capable of effectively prompting a user to improve to reach a target relating to the body.

BRIEF DESCRIPTION OF DRAWINGS

FIG. 16 is a diagram illustrating an example of intervention effectiveness performance of a group according to this embodiment.

FIG. 18 is a first diagram for describing the process of calculating an intervention threshold using performance of a group in this embodiment.

FIG. 20 is a diagram illustrating an example of intervention effectiveness performance of an individual according to this embodiment.

FIG. 22 is a first diagram for describing the process of calculating an intervention threshold using performance of an individual in this embodiment.

DESCRIPTION OF EMBODIMENTS

Figure 1:
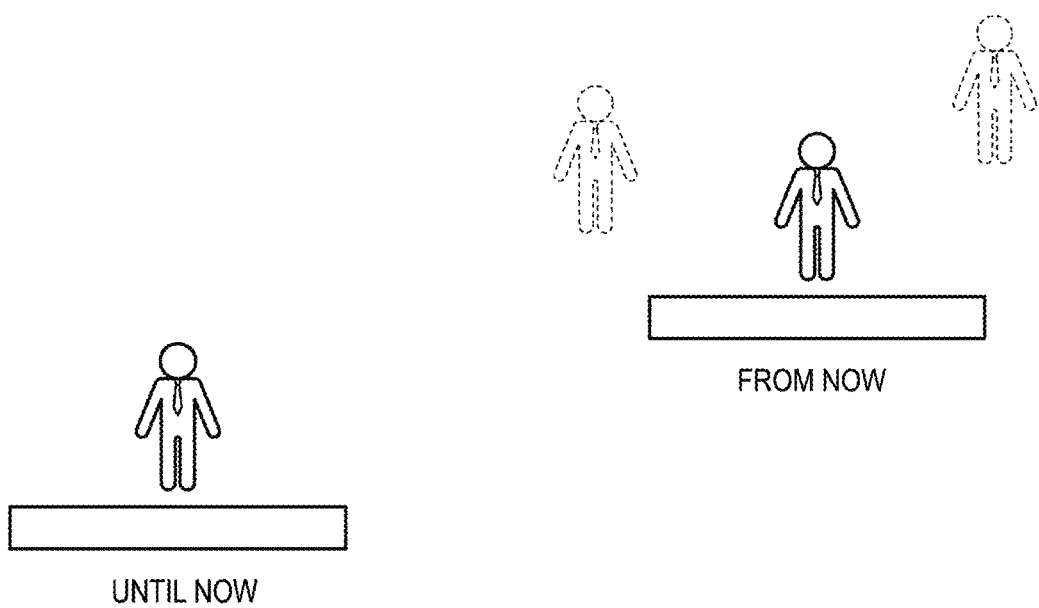
FIG. 1 is a diagram illustrating procedure 1 for improving a habit.

Embodiments of a target management system will be described below with reference to the drawings. In the following description, like parts and components are given like reference numerals. Names and functions thereof are also the same. Thus, description of such components is not repeated.

Concept

"Improving a habit" is to change their lifestyle from what was thought to be "normal" until now to a desired state, and subsequently make to recognize this desired lifestyle as the new "normal" from now. The process for achieving "improving a habit" can be described as follows. (1) Perceive what kind of state this "from now" desired normal will look like. (2) Understand what change is needed from the "until now" normal. (3) Surely make small change that don't burden themselves. (4) Come to recognize the achieved "from now" desired state as their normal.

FIG. 1 to FIG. 9 are diagrams illustrating procedure 1 to procedure 9 for improving a habit. Referring to FIG. 1, value is converted to a numerical value in procedure 1. In other words, when a target self is determined, a target numerical value of a predetermined index needed to achieve the target is specified.

Figure 2:
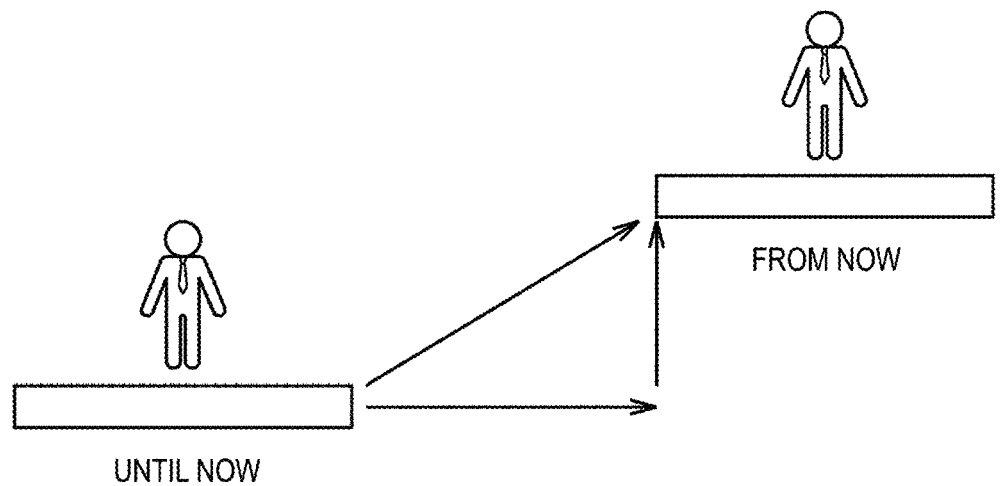
FIG. 2 is a diagram illustrating procedure 2 for improving a habit.

Referring to FIG. 2, in procedure 2, the amount of change needed to reach the value is calculated. In other words, the amount of change is calculated by establishing the difference between the target numerical value and the current value and the time needed to achieve the target.

Figure 3:
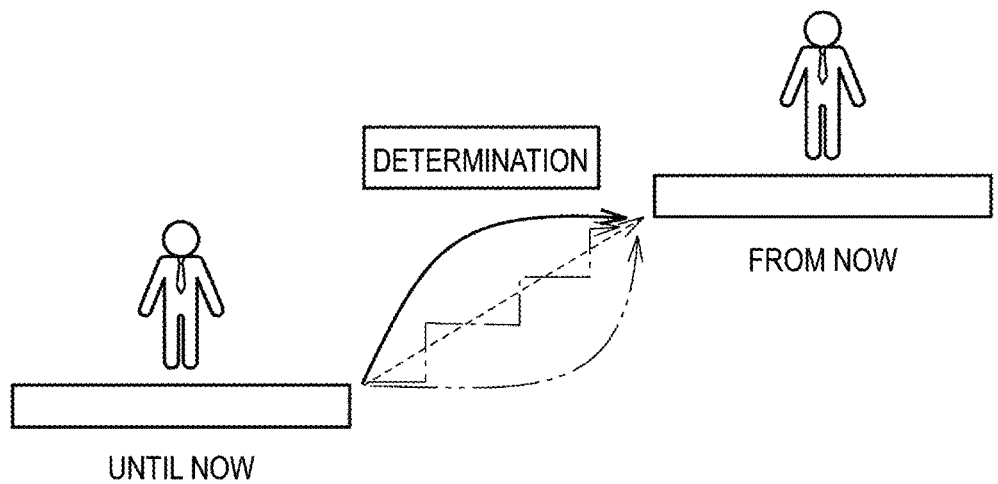
FIG. 3 is a diagram illustrating procedure 3 for improving a habit.

Referring to FIG. 3, in procedure 3, an achievement route for change is presented. In other words, a plurality of routes to achieve the same amount of change are presented and determine which of the plurality of route is selected. "Route" is the transition in value of the predetermined index to the target numerical value of the predetermined index.

Figure 4:
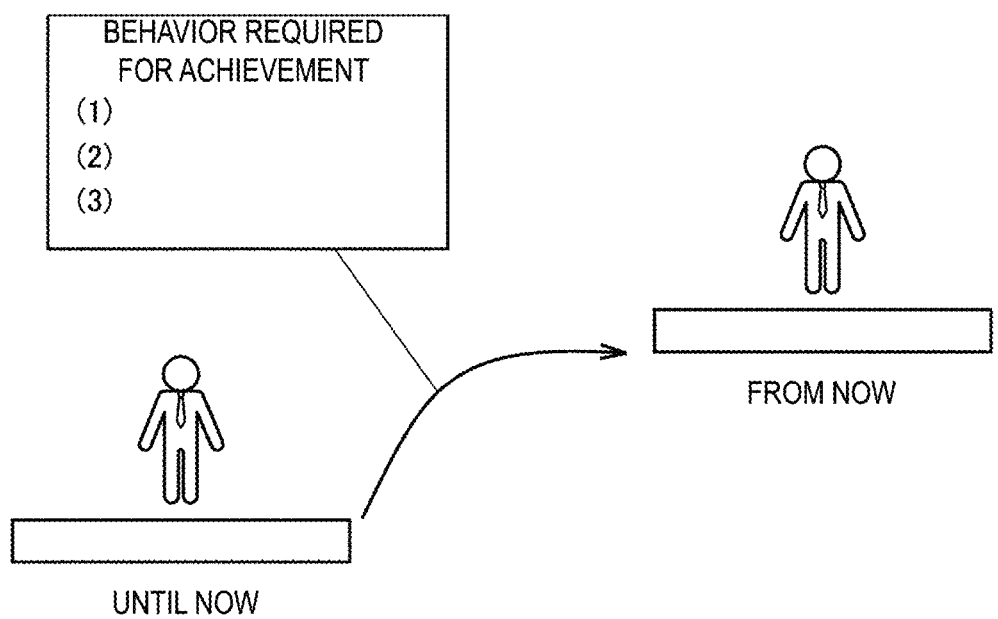
FIG. 4 is a diagram illustrating procedure 4 for improving a habit.

Referring to FIG. 4, in procedure 4, a specific behavior to progress the route is presented. In other words, a specific behavior required to follow the assumed route is presented.

Figure 5:
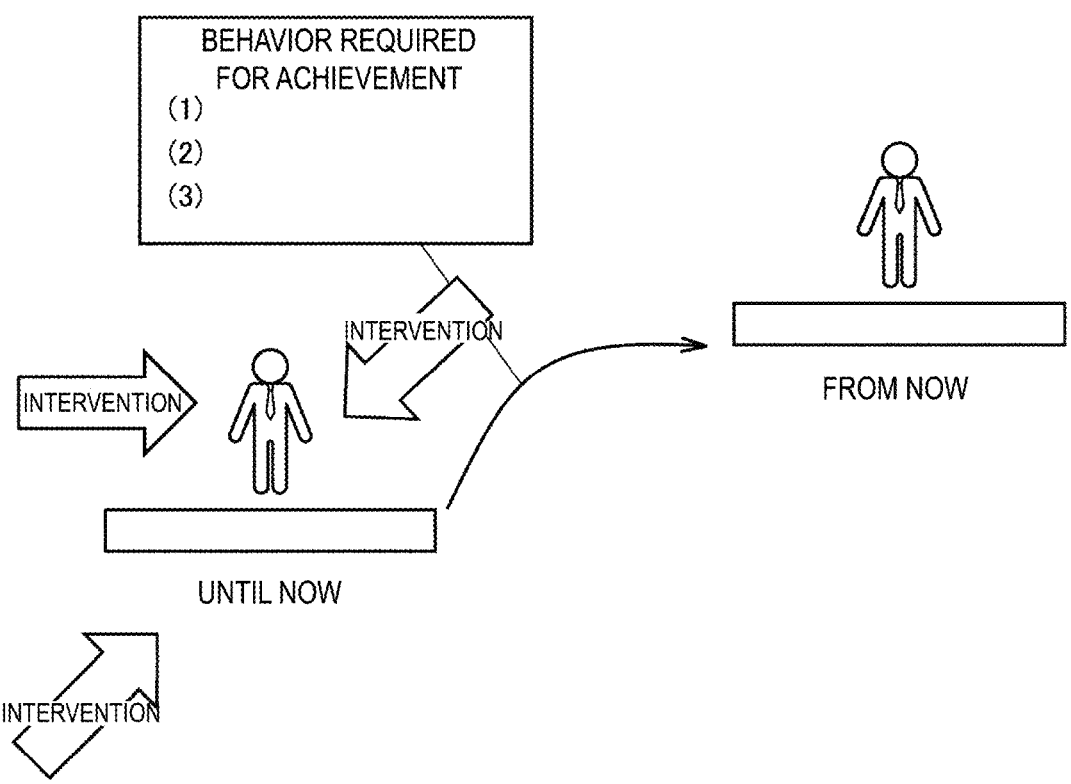
FIG. 5 is a diagram illustrating procedure 5 for improving a habit.

Referring to FIG. 5, in procedure 5, appropriate intervention is provided in an appropriate manner. In other words, to promote sure practice of the behavior, the appropriate content, time, location, and route are selected and provided.

Figure 6:
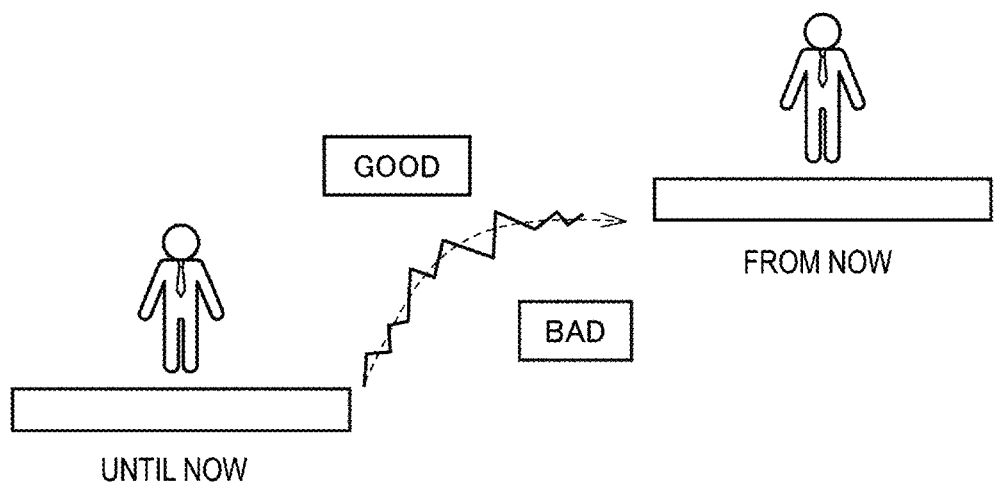
FIG. 6 is a diagram illustrating procedure 6 for improving a habit.

Referring to FIG. 6, in procedure 6, daily progress is checked, and feedback is performed. In other words, interventions and a situation of daily progress according to the interventions are compared against the determined route and evaluated. Depending on the situation of the progress, intervention content, change speed, and the like are changed.

Figure 7:
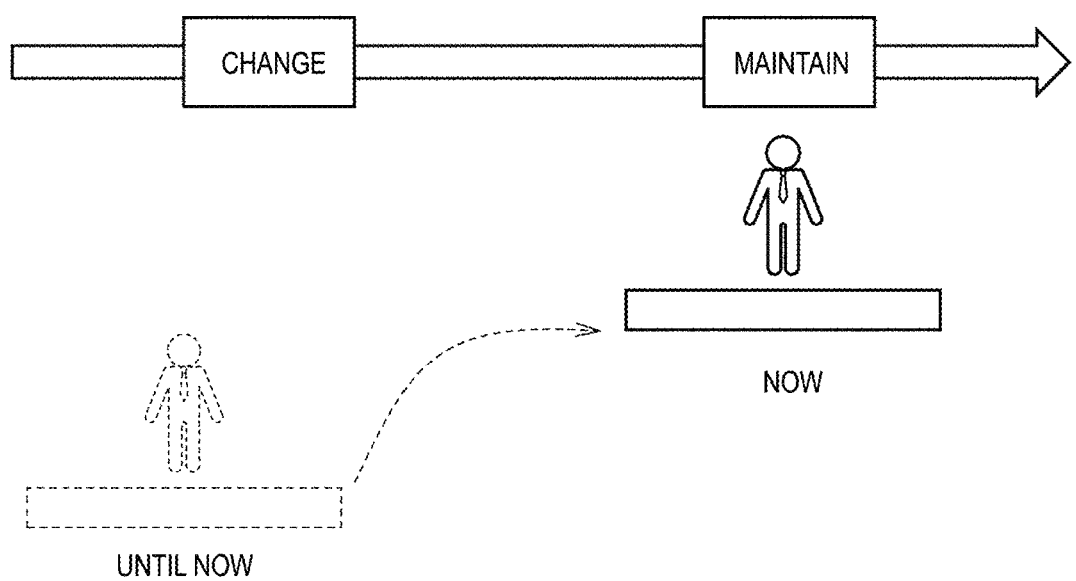
FIG. 7 is a diagram illustrating procedure 7 for improving a habit.

Referring to FIG. 7, in procedure 7, the stage achievement judgment and intervention strategy are changed. In other words, when the target self is reached, the phase is switched and the treatment policy is changed to "maintain".

Figure 8:
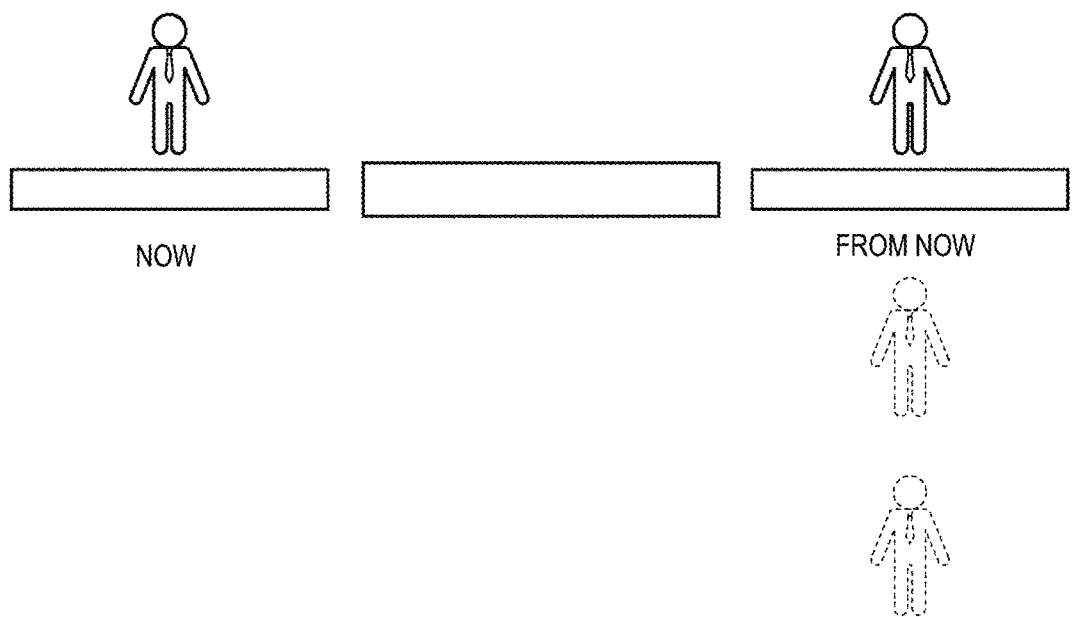
FIG. 8 is a diagram illustrating procedure 8 for improving a habit.

Referring to FIG. 8, in procedure 8, a future degression assumption and a route selection is performed. In other words, in light of the future assumed to change depending on a behavior state from now, whether to maintain the current state or change slightly is selected.

Figure 9:
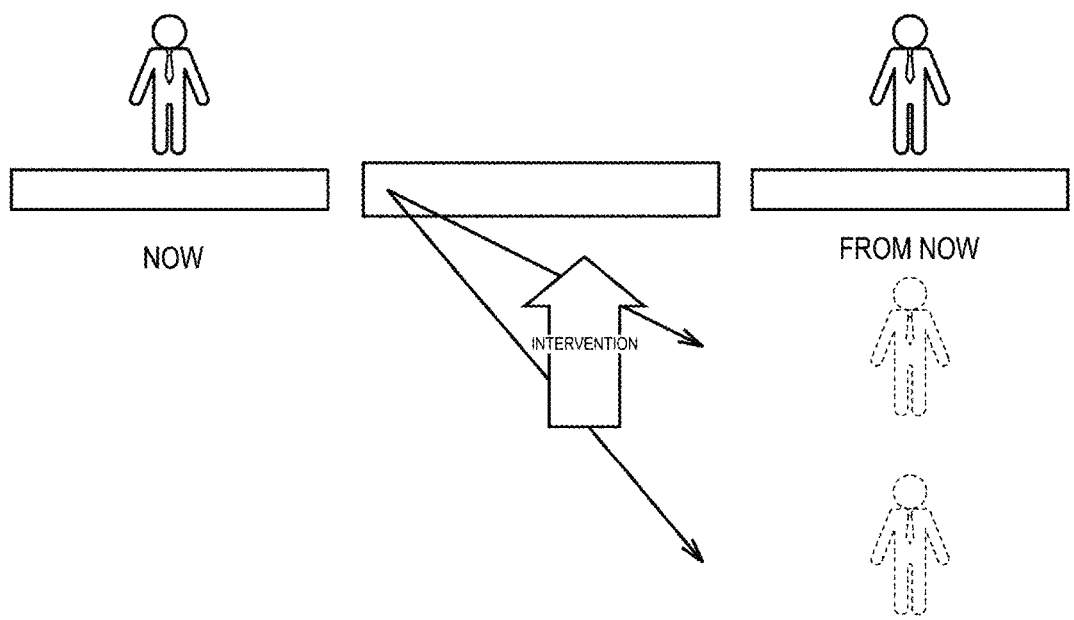
FIG. 9 is a diagram illustrating procedure 9 for improving a habit.

Referring to FIG. 9, in procedure 9, intervention is performed to slow down the degression speed. In other words, a change likely away from a maintained state is predicted beforehand, and intervention to circumvent the change and praise for maintaining the state are given.

Target Management System

Figure 10:
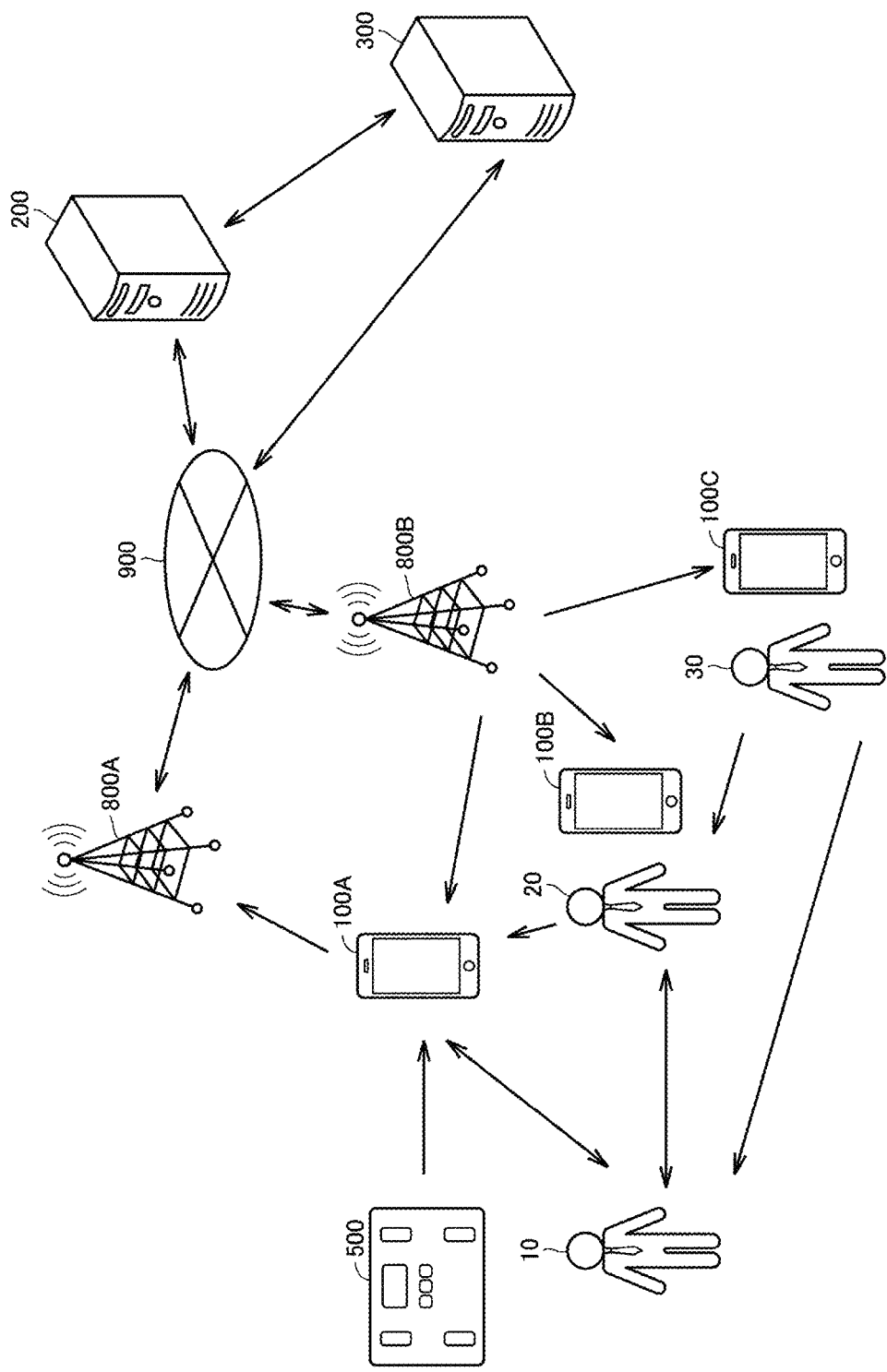
FIG. 10 is a schematic diagram illustrating the overall configuration of a target management system according to this embodiment.

FIG. 10 is a schematic diagram illustrating the overall configuration of a target management system according to this embodiment. Referring to FIG. 10, the target management system includes information communication terminals 100A to 100C (e.g., a smartphone, mobile phone, personal computer (PC), tablet PC, or the like) respectively owned by users 10, 20 and 30, a server 200 configured for target management, the other server 300, a measuring device 500 of biological information, and communication facilities 800A and 800B of a telecommunications provider that provide communication between information communication terminals.

The servers 200 and 300 and the communication facilities 800A and 800B are communicatively connected to one another via a communication network 900, for example, a public network such as the Internet or a public communication network or a private network such as a local area network (LAN). The information communication terminals 100A and 100B and the communication facilities 800A and 800B are communicatively connected to one another via wireless communication.

Figure 11:
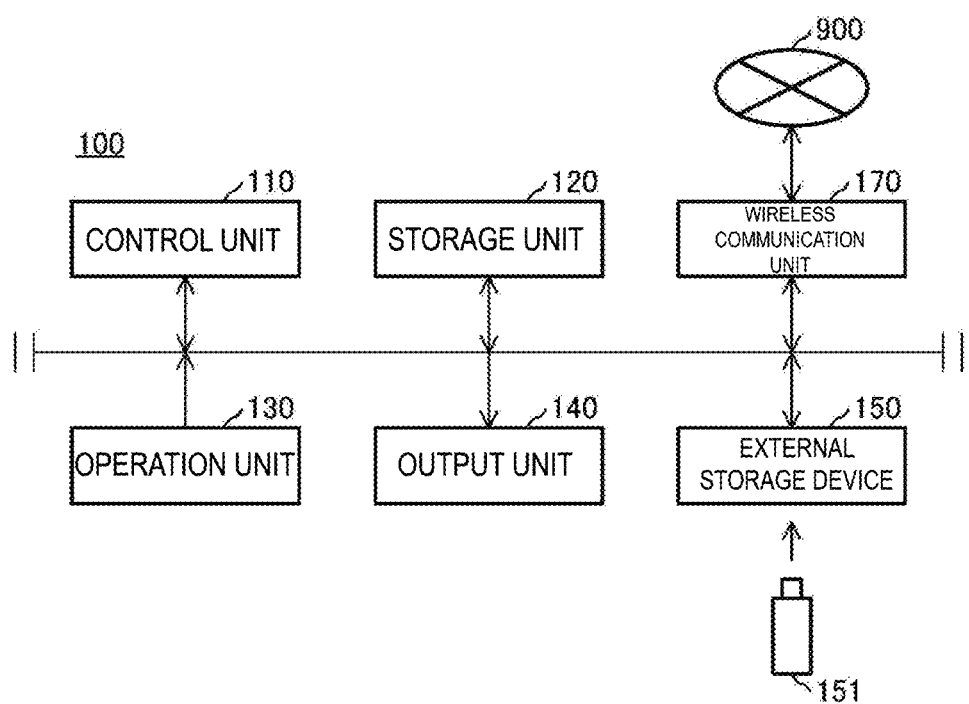
FIG. 11 is a block diagram illustrating the configuration of an information communication terminal according to this embodiment.

FIG. 11 is a block diagram illustrating the configuration of an information communication terminal 100 according to this embodiment. Referring to FIG. 11, the information communication terminal 100 includes a control unit 110 configured to control all of the information communication terminal 100, a storage unit 120 configured to store predetermined information, an operation unit 130, an output unit 140, an external storage device 150, and a wireless communication unit 170. Note that, although not illustrated, the information communication terminal 100 includes other components such as a sound input/output unit configured to input/output sound.

The control unit 110 includes a central processing unit (CPU) and an auxiliary circuit thereof and controls the storage unit 120, the operation unit 130, the output unit 140, and the wireless communication unit 170. The control unit 110 also executes a predetermined process according to a program or data stored in the storage unit 120, processes data input from the operation unit 130 and the wireless communication unit 170, stores processed data in the storage unit 120, outputs processed data to the output unit 140 and the wireless communication unit 170, and the like.

The storage unit 120 includes random access memory (RAM) used as the working area need for the control unit 110 to execute a program and read-only memory (ROM) configured to store a program for the control unit 110 to execute. In the RAM, a program and data for executing a predetermined process is read from the operation unit 130, the wireless communication unit 170, or the external storage device 150 and stored. Furthermore, a hard disk drive or memory card may be used as an auxiliary storage device to supplement the storage area of the RAM.

The external storage device 150 is configured to includes a memory card reader/writer. The external storage device 150 electrically records predetermined data or a program received from the control unit 110 to a recording medium 151, such as a memory card or universal serial bus (USB) memory, reads from the recording medium 151 and relays it to the control unit 110. Note that the external storage device 150 may be configured to include a recording device such as a hard disk drive, a flexible disk drive, a magneto-optical (MO) disk drive, a compact disc (CD) drive, or a digital versatile disc (DVD) drive.

The operation unit 130 includes a touch panel and/or operation buttons configured to input numbers, such as phone numbers, various data, alphabetical characters and other characters, and the like. Note that the operation unit 130 may include a portion for other operations. When the operation unit 130 is given an operation by a user, an operation signal corresponding to the operation is sent from the operation unit 130 to the control unit 110. The control unit 110 controls each of the components of the information communication terminal 100 according to the operation signal received from the operation unit 130.

The wireless communication unit 170 is controlled by the control unit 110 and receives a wireless signal from an information communication terminal 100 or a fixed telephone of another party of communication via a communication facility 800 of a telecommunications provider and an antenna, converts the received wireless signal to a sound signal, and sends the converted sound signal to the sound input/output unit. The wireless communication unit 170 also converts a sound signal from the sound input/output unit to a wireless signal and sends the converted wireless signal to the information communication terminal 100 or the fixed telephone of another party of communication via the communication facility 800 of the telecommunications provider and the antenna.

Also, the wireless communication unit 170 is controlled by the control unit 110 and, for example, receives a wireless signal via a device capable of data communication such as a server or another information communication terminal 100 and a communication facility 800 of a telecommunications provider and an antenna, converts the received wireless signal to data and stores the converted data in the storage unit 120, and sends the data to the output unit 140 to be displayed. The wireless communication unit 170 also converts data for sending to a wireless signal and sends the converted wireless signal to a data communication destination server or another information communication terminal 100 via the communication facility 800 of the telecommunications provider and the antenna.

The wireless communication unit 170 is controlled by the control unit 110 and exchanges data with another device capable of network communication, such as a server or another information communication terminal 100, via a public wireless LAN or a private network wireless LAN.

The output unit 140 includes a display and a speaker. The output unit 140 is controlled by the control unit 110 and outputs a video signal or a sound signal that are converted by the control unit 110 from information received by the wireless communication unit 170, information stored in the storage unit 120, or information read from the recording medium 151 by the external storage device 150, respectively as an image displayed on a display or as sound output from a speaker.

Figure 12:
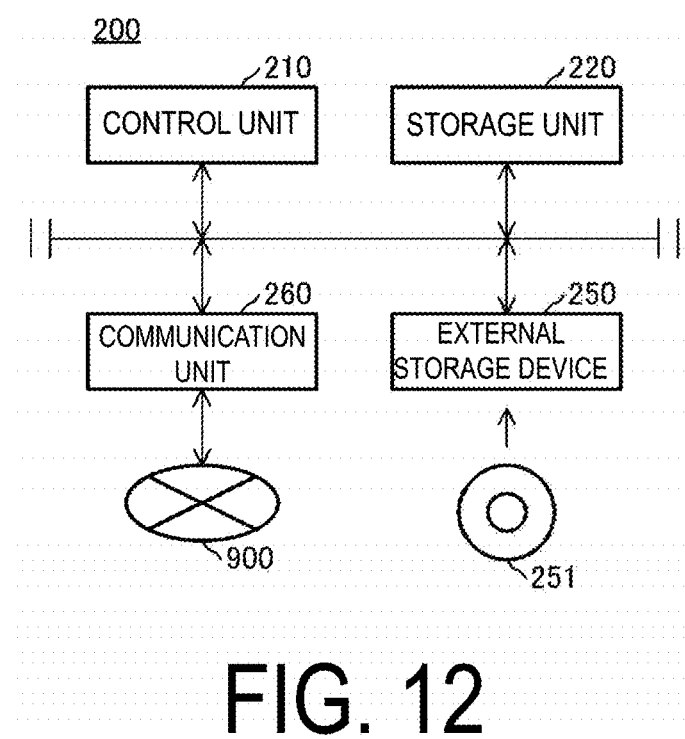
FIG. 12 is a block diagram illustrating the configuration of a server for target management according to this embodiment.

FIG. 12 is a block diagram illustrating the configuration of the server 200 for target management according to this embodiment. Referring to FIG. 12, the server 200 includes a control unit 210 configured to control all of the server 200, a storage unit 220 configured to store predetermined information, an external storage device 250 configured to supplement the storage unit 220 and store predetermined information, and a communication unit 260 configured to communicate with an external device via the communication network 900.

The storage unit 220 has a similar configuration to that of the storage unit 120 of the information communication terminal 100 illustrated in FIG. 11, and thus redundant descriptions thereof will not be repeated.

The communication unit 260 sends and receives data to and from an external device via the communication network 900 in a predetermined protocol. The communication unit 260 sends data received from the control unit 210 to an external device and relays data received from an external device to the control unit 210.

The external storage device 250 is configured to include a storage device such as a hard disk drive, a flexible disk drive, a MO drive, a CD drive, a DVD drive, or a memory card reader/writer. The external storage device 250 magnetically, optically, or electrically records predetermined data or a program received from the control unit 210 to a recording medium 251, reads from the recording medium 251 and relays the predetermined data or the program to the control unit 210.

Examples of the recording medium 251 include a magnetic disk, such as a hard disk, a flexible disk, an optical disc, such as a Compact Disc Read Only Memory (CD-ROM), a Compact Disc Recordable (CD-R), a Compact Disc ReWritable (CD-RW), a Digital Versatile Disc Read Only Memory (DVD-ROM), a Digital Versatile Disc Recordable (DVD-R), a Digital Versatile Disc Rerecordable Disc (DVD-RW), a Digital Versatile Disc Random Access Memory (DVD-RAM), a DVD+R, a Digital Versatile Disc ReWritable (DVD+RW), a Blu-ray (trade name) Disc Recordable (BD-R), a Blu-ray (trade name) Disc Rewritable (BD-RE), a Blu-ray (trade name) Disc Read Only Memory (BD-ROM), a magneto-optical disk such as a MO, a memory card, a USB memory, and the like.

The control unit 210 has the similar configuration as the control unit 110 of the information communication terminal 100 illustrated in FIG. 11. The control unit 210 controls the storage unit 220, the external storage device 250, and the communication unit 260, executes a predetermined process according to a program or data stored in the storage unit 220, processes data input from the external storage device 250 or the communication unit 260, stores processed data in the storage unit 220 or the recording medium 251 of the external storage device 250 and outputs the processed data from the communication unit 260, and the like.

Note that in this embodiment, the server 200 does not includes an operation unit and a display unit, is operated by an operation from an operation unit of an external device, and outputs information to a display unit of an external device. However, no such limitation is intended, and the server 200 may include as part of its configuration an operation unit and a display unit. The operation unit may include a keyboard and a mouse and may relay to the control unit 210 an operation signal indicating the operation contents input to the server 200 by an operation of the keyboard and the mouse of the operation unit. The display unit may include a display, and the display may display an image corresponding to image data received from the control unit 210.

Note that the other server 300 has a similar configuration to that of the server 200, and thus redundant descriptions thereof will not be repeated.

Figure 13:
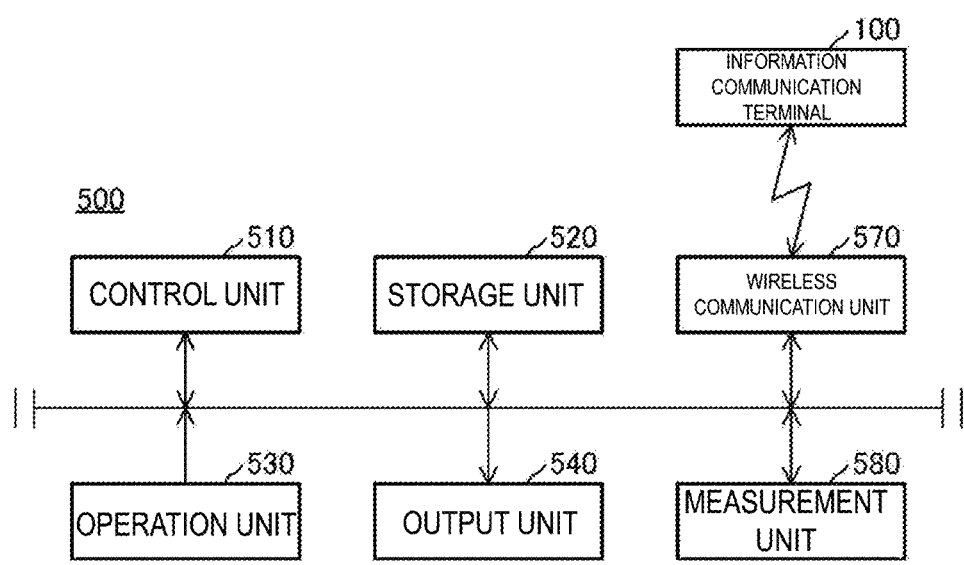
FIG. 13 is a block diagram illustrating the configuration of a measuring device of biological information according to this embodiment.

FIG. 13 is a block diagram illustrating the configuration of the measuring device 500 of biological information according to this embodiment. Referring to FIG. 13, the measuring device 500 of biological information, such as the body composition meter illustrated in FIG. 13, includes a control unit 510 configured to control all of the measuring device 500, a storage unit 520 configured to store predetermined information, an operation unit 530, an output unit 540, a wireless communication unit 570, and a measurement unit 580.

The control unit 510, the storage unit 520, the operation unit 530, the output unit 540, and the wireless communication unit 570 respectively have a similar configuration to that of the control unit 110, the storage unit 120, the operation unit 130, the output unit 140, and the wireless communication unit 170 of the information communication terminal 100 illustrated in FIG. 11, and thus redundant descriptions thereof will not be repeated. Note that the wireless communication unit 570 may be capable of directly communicating with the information communication terminal 100 and may be capable of communicating via the communication network 900 or the communication facility 800 of a telecommunications provider.

The measurement unit 580 is controlled by the control unit 110 and measures predetermined biological information from among a plurality of biological information of a user and sends information of the measurement results to the control unit 110. Biological information includes information indicating the state of the living body and information indicating physical activity and movement, and specifically includes every indices relating to the living body, such as body weight, chest circumference, waist circumference, height, body composition values (body fat percentage, visceral fat level, subcutaneous fat percentage, basal metabolism, skeletal muscle percentage, muscle percentage, BMI, body age, and other values indicating body composition), amount of activity, step count, blood pressure value, heartbeat (pulse), body temperature, respiration rate, index values relating to blood (blood glucose value, neutral fat level, cholesterol level, and the like), calorie consumption, food intake, water intake, excretion amount, sweat amount, lung capacity, sleep amount, and the like.

Figure 14:
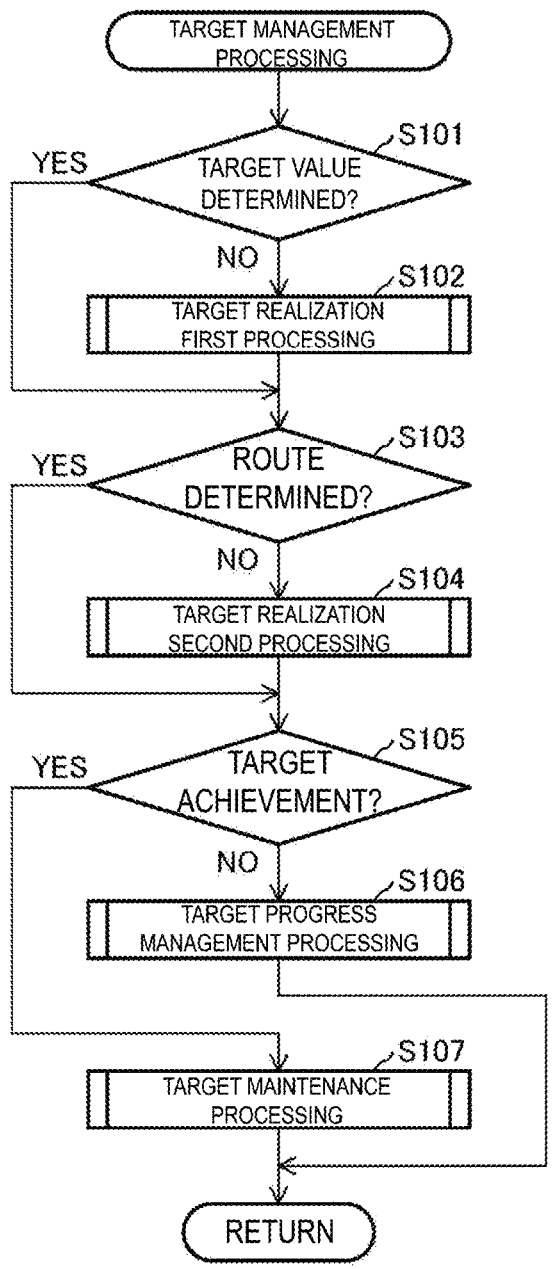
FIG. 14 is a flowchart illustrating the target management processing flow executed by the server for target management according to this embodiment.

FIG. 14 is a flowchart illustrating the target management processing flow executed by the server 200 for target management according to this embodiment. Referring to FIG. 14, the control unit 210 of the server 200 assesses whether a target value for improvement of biological information has already been determined (step S101). If it is assessed that the target value has not been determined (NO in step S101), the control unit 210 executes target realization first processing (step S102).

If it is assessed that the target value has been determined (YES in step S101), and after step S102, the control unit 210 assesses whether the route to reach the target has already been determined (step S103). If it is assessed that the route has not been determined (NO in step S103), the control unit 210 executes target realization second processing (step S104).

If it is assessed that the route has been determined (YES in step S103), and after step S104, the control unit 210 assesses whether the set target has already been reached (step S105). If it is assessed that the target has not been reached (NO in step S105), the control unit 210 executes the target progress management processing illustrated in FIG. 15 below (step S106).

If it is assessed that the target has been reached (YES in step S105), the control unit 210 executes target maintenance processing (step S107).

Target Progress Management Processing

Figure 15:
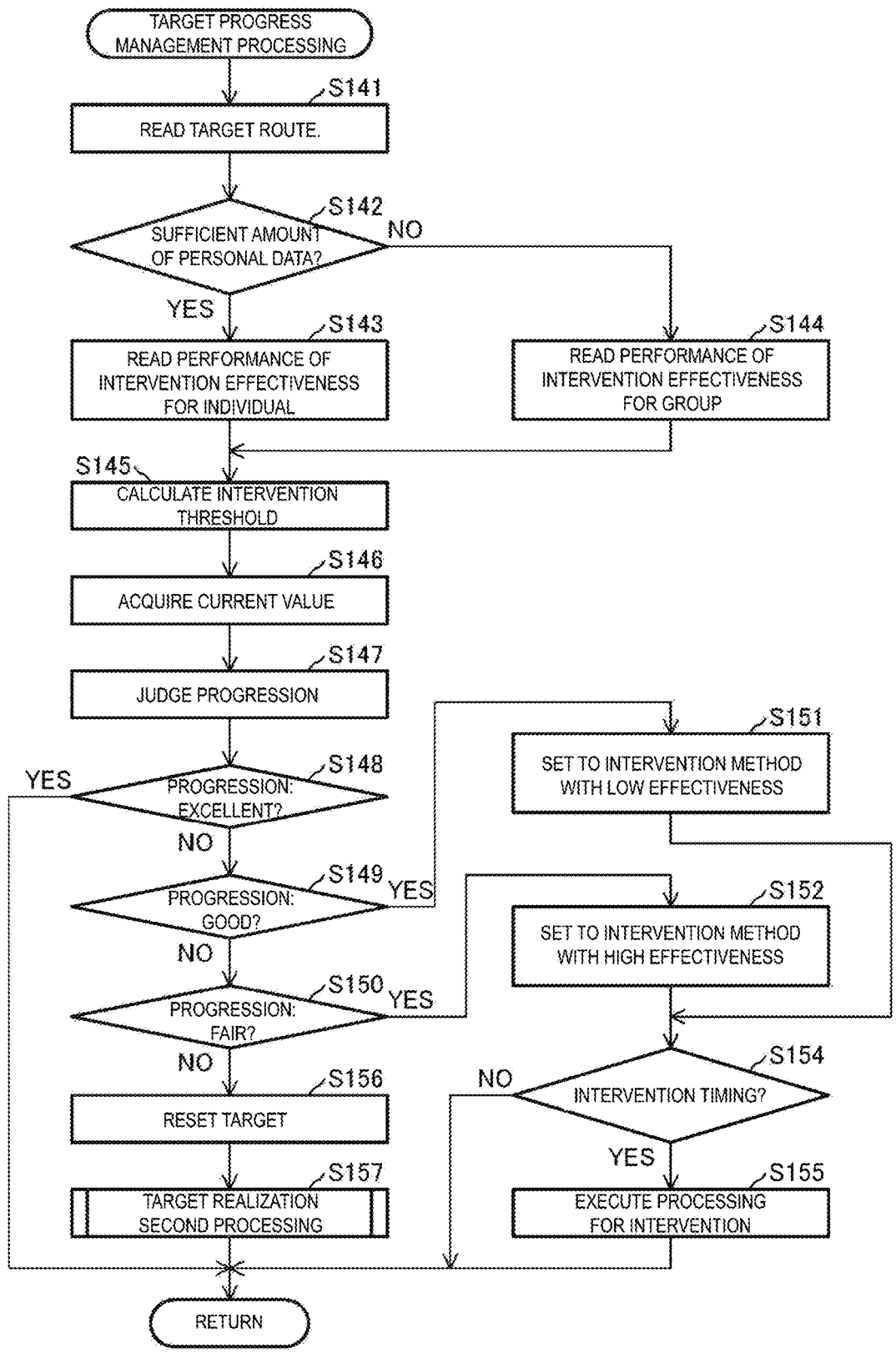
FIG. 15 is a flowchart illustrating the target progress management processing flow executed by the server for target management according to this embodiment.

FIG. 15 is a flowchart illustrating the target progress management processing flow executed by the server 200 for target management according to this embodiment. Referring to FIG. 15, the control unit 210 of the server 200 reads a target route stored in the storage unit 220 (step S141).

Next, the control unit 210 assesses whether a sufficient amount of personal data involving intervention performance has been collected (for example, a number greater than or equal to the number required to calculate statistics) (step S142). If it is assessed that the sufficient amount of personal data has been collected (YES in step S142), the control unit 210 reads the intervention effectiveness performance of the user 10 collected in the storage unit 220 (step S143). If it is assessed that the sufficient amount of personal data has not been collected (NO in step S142), the control unit 210 reads the intervention effectiveness performance of a group collected in the storage unit 220 (step S144).

Then, the control unit 210 calculates an intervention threshold and intervention method using the performance of the read intervention effectiveness performance (step S145).

FIG. 16 is a diagram illustrating an example of intervention effectiveness performance of a group according to this embodiment. Referring to FIG. 16, for all of the users of the target management system, information indicating the intervention effectiveness, such as the effective intervention method and whether the final target was reached are associated with the set target index, gender, age, family composition, and the like and collected in the storage unit 220.

Figure 17:
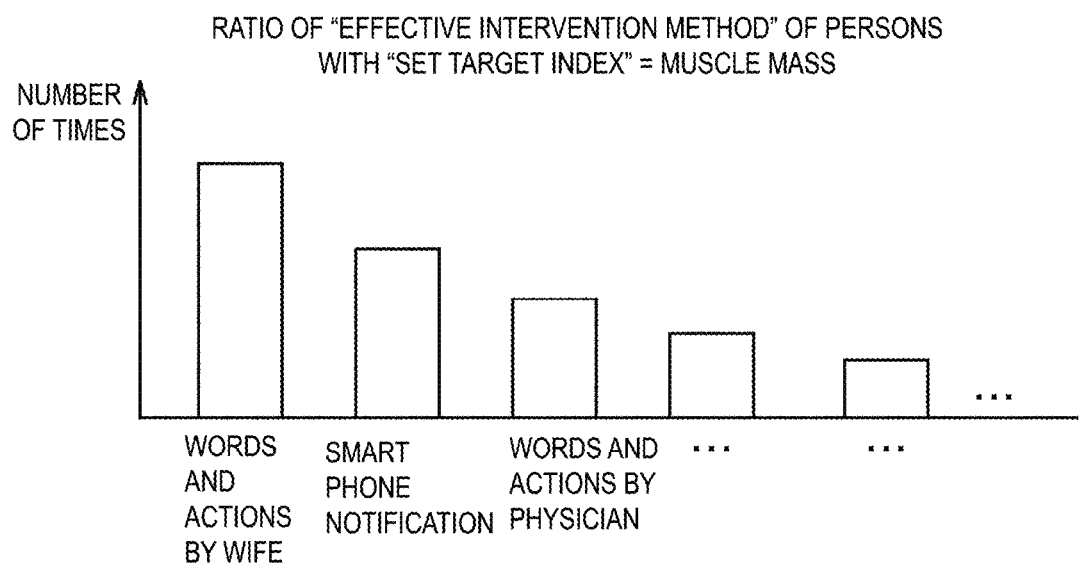
FIG. 17 is a diagram for describing the process of calculating an intervention method using performance of a group in this embodiment.

FIG. 17 is a diagram for describing the process of calculating an intervention method using performance of a group in this embodiment. Referring to FIG. 17, from the intervention effectiveness performance of the group listed in FIG. 16, the "final target" being "reached" is aggregated for each "set target index". In this example, order of the number of times in the "effective intervention method" for persons with the same "set target index", which is muscle mass, as the user 10, is that the highest is words and actions by wife, followed by notification via smart phone, then words and actions by physician. In this example, an effective intervention method is calculated for the user 10 from the performance of users with the same target index as the user 10.

Note that here, as an intervention method for the user 10, a statistically effective intervention method is calculated from the intervention methods for persons with the same target index as the user 10. However, no such limitation is intended, and as an intervention method for the user 10, a statistically effective intervention method may be determined from the intervention methods for persons with a similar target index to the user 10. A similar target index is pre-stored in the storage unit 220. For example, the body fat percentage, the visceral fat level, and the subcutaneous fat percentage are stored labeled as being similar to one another.

Also, in the present embodiment, as an intervention method for the user 10, a statistically effective intervention method is determined from the intervention methods for persons with target index that is a similar type of target index to the user 10. However, as an intervention method for the user 10, a statistically effective intervention method may be determined from the intervention methods for persons with target index that is a similar type of target index and a similar value to the user 10. A range for similar target index values is pre-stored in the storage unit 220. For example, a range of similar target index value for weight is ±10% of the weight is stored.

FIG. 18 is a first diagram for describing the process of calculating an intervention threshold using performance of a group in this embodiment. Referring to FIG. 18, from the intervention effectiveness performance of the group listed in FIG. 16, the same "set target index" as that of the user 10 (in this example, "weight") is extracted. Then, the transition in the target index of persons that reached their target from among the extracted users is read from a database collected in the storage unit 220, and a threshold is statistically calculated.

Figure 19:
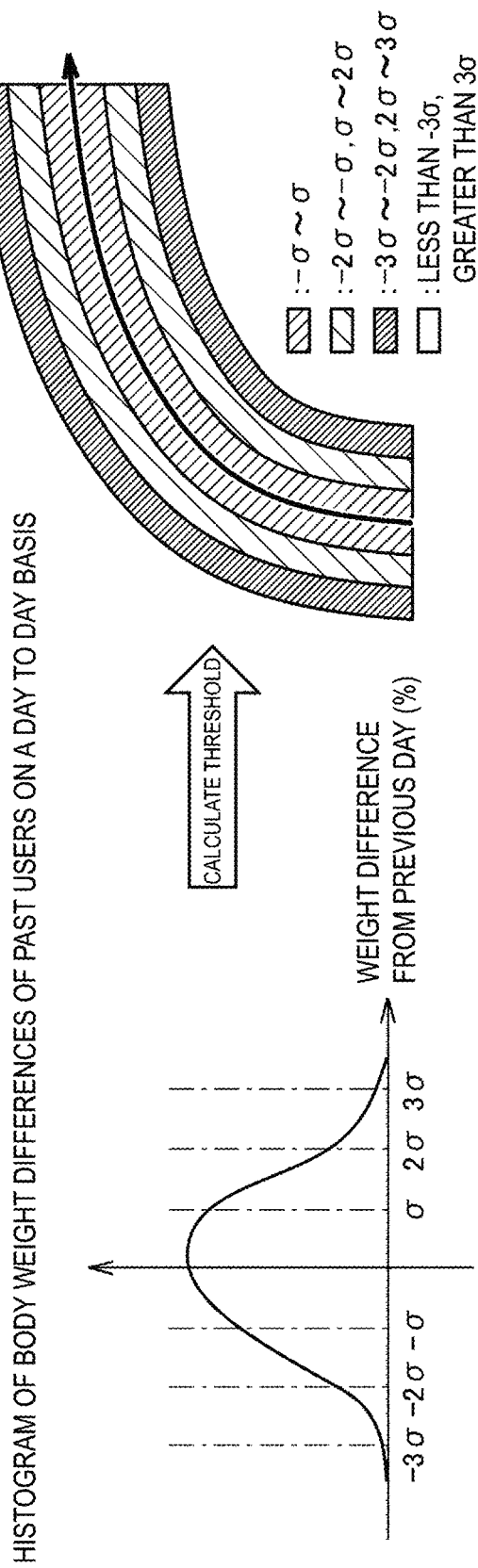
FIG. 19 is a second diagram for describing the process of calculating an intervention threshold using performance of a group in this embodiment.

FIG. 19 is a second diagram for describing the process of calculating an intervention threshold using performance of a group in this embodiment. Referring to FIG. 19, as a method of statistically calculating a threshold, first, a histogram of the target index of the read users is created using the body weight difference from yesterday on a day to day basis. A standard deviation a in the histogram is then calculated. Then, for the value of the index of the target route of the user 10, intervention thresholds $-\sigma$, $-2\sigma$, $-\sigma$, $+\sigma$, $+2\sigma$, $+3\sigma$ are found. In this manner, an intervention threshold for the user 10 is calculated from the performance of users with the same target index as the user 10.

FIG. 20 is a diagram illustrating an example of intervention effectiveness performance of an individual according to this embodiment. Referring to FIG. 20, for each user of the target management system, information indicating the intervention effectiveness, such as the intervention time, intervention method, and presence of intervention effect are associated and collected in the storage unit 220.

Figure 21:
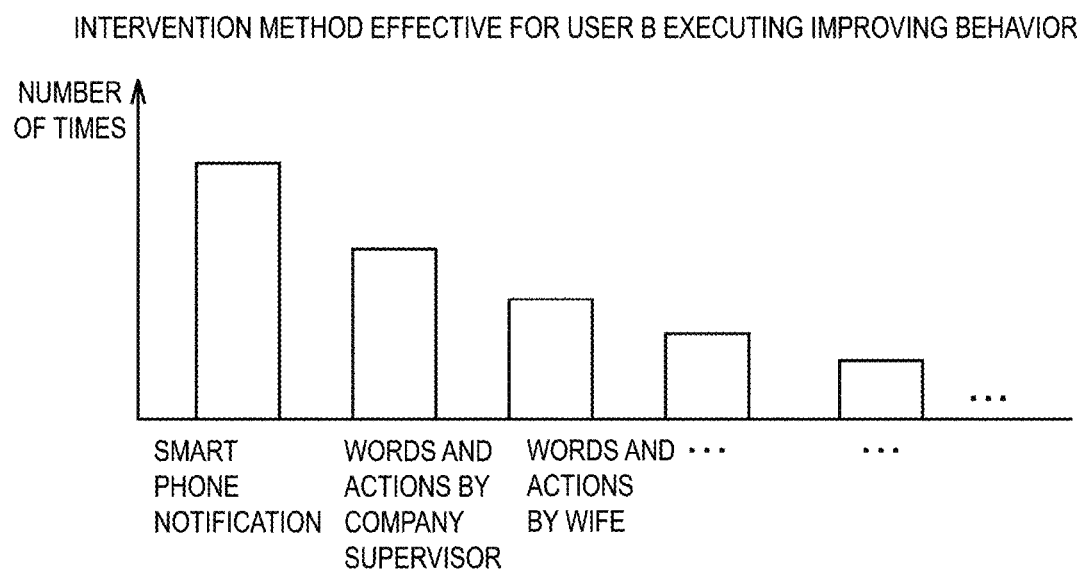
FIG. 21 is a diagram for describing the process of calculating an intervention method using performance of an individual in this embodiment.

FIG. 21 is a diagram for describing the process of calculating an intervention method using performance of an individual in this embodiment. Referring to FIG. 21, from the intervention effectiveness performance of an individual listed in FIG. 20, number of times of effective intervention is aggregate for each intervention method. In this example, order of the number of times in intervention method, which was effective in user B improving the behavior, is that the highest is notification via smart phone, followed by words and actions by a company supervisor, then words and actions by wife. In this example, an effective intervention method is statistically calculated for the user 10 from the performance of the user 10.

FIG. 22 is a first diagram for describing the process of calculating an intervention threshold using performance of an individual in this embodiment. Referring to FIG. 22, when the target index of the user 10 is weight, the transition in the target index of the user 10 is read from a database collected in the storage unit 220, and a threshold is statistically calculated.

Figure 23:
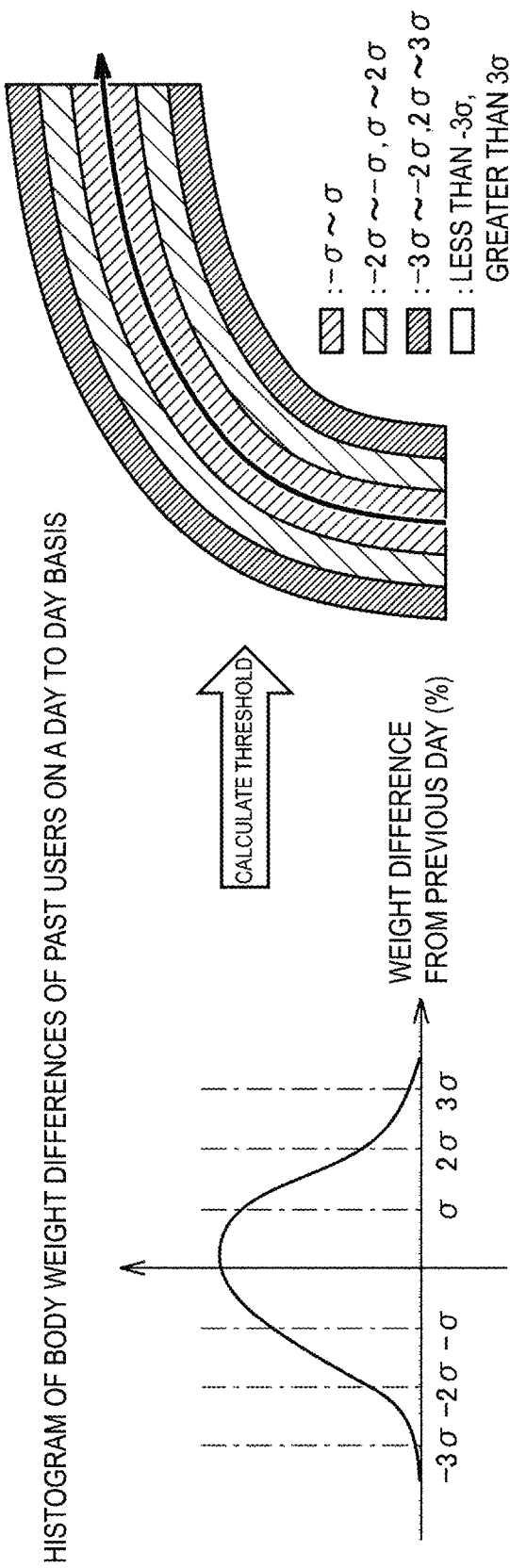
FIG. 23 is a second diagram for describing the process of calculating an intervention threshold using performance of an individual in this embodiment.
Figure 24A:
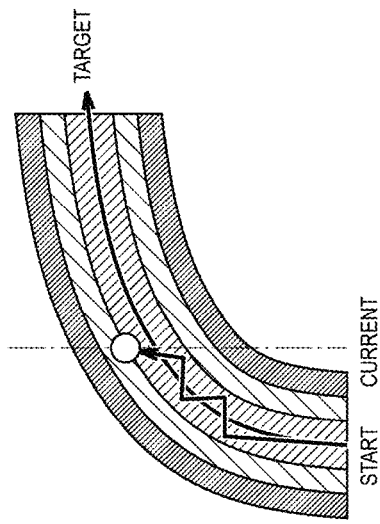
FIGS. 24A to 24D are diagrams for describing the progression of the target management in this embodiment.
Figure 24B:
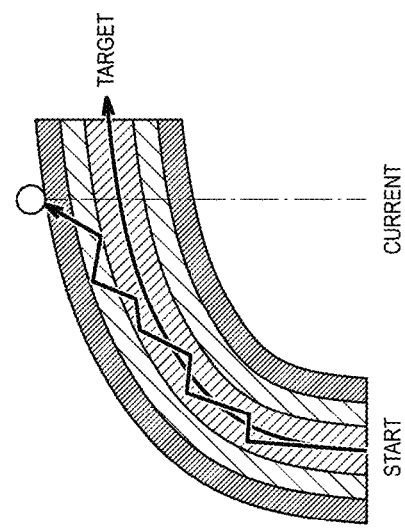
Figure 24C:
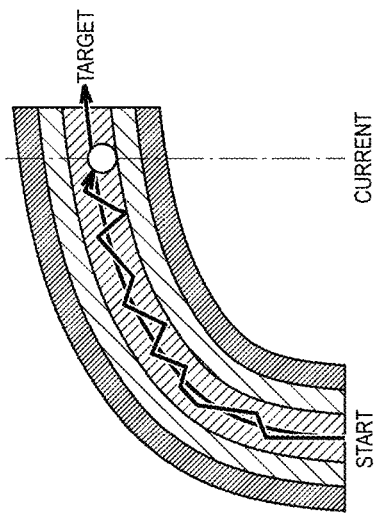
Figure 24D:
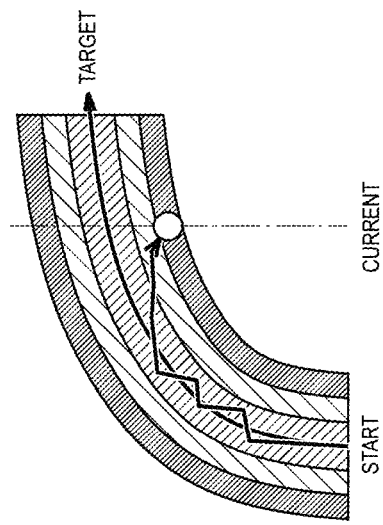

FIG. 23 is a second diagram for describing the process of calculating an intervention threshold using performance of an individual in this embodiment. Referring to FIG. 23, as a method of statistically calculating a threshold, first, a histogram of the target index of the user 10, which was read, is created using the body weight difference from yesterday on a day to day basis. A standard deviation a in the histogram is then calculated. Then, for the value of the index of the target route of the user 10, intervention thresholds $-3\sigma$, $-2\sigma$, $-\sigma$, $+\sigma$, $+2\sigma$, $+3\sigma$ are found. In this manner, an intervention threshold for the user 10 is calculated from the performance of the user 10.

Returning to FIG. 15, the control unit 210 obtains the current value of the index of the user 10 (step S146).

Specifically, the control unit 210 obtains, from the information communication terminal 100A, the current value of the index of the user 10 input into the information communication terminal 100A by the user 10, and the current value of the index of the user 10 obtained from the measuring device 500 by the information communication terminal 100A.

Next, the control unit 210 compares the obtained current value of the user 10 and the current value of the index of the target route of the user 10 and judges the degree of divergence of the current value of the index of the user 10 to be in an "ideal range" if it is between −σ and σ, in a "permissible range" if it is between −2σ and −σ or between σ and 2σ, in a "limit range" if it is between −3σ and −2σ or between 2σ and 3σ, and in a "failure range" if it is less than −3σ or more than 3σ. From this, the control unit 210 judges the progression of the target management of the user 10 (step S147). Specifically, when the degree of divergence is judged to be in the "permissible range", the "limit range", and the "failure range", the progression is judged as being "excellent", "good", and "fair", respectively.

Note that the degree of divergence is not limited to being expressed in stepwise terms such as "permissible range", "limit range", and "failure range", and it is only required that the degree of divergence between the current value of the index of the user 10 and the current value of the index of the target route of the user 10 is expressed. For example, the difference in value between the current value of the index of the user 10 and the current value of the index of the target route of the user 10 may be expressed, or a ratio of the current value of the index of the user 10 against the current value of the index of the target route of the user 10 may be expressed.

FIGS. 24A to 24D are diagrams for describing the progression of the target management in this embodiment. Referring to FIG. 24A to 24D, FIGS. 24A to 24D illustrate the progression of the target management of the user 10, i.e., the current value of the index of the user 10, is in the "ideal range", the "permissible range", the "limit range", and the "failure range", respectively.

Returning to FIG. 15, the control unit 210 assesses whether the progression is "excellent", i.e., whether the current value of the index of the user 10 is in the "ideal range" (step S148). If it is determined to be "excellent" (YES in step S148), the control unit 210 returns the executing process to the call source of the process.

If it assessed to be not "excellent" (NO in step S148), the control unit 210 assesses whether the progression is "good", i.e., whether the current value of the index of the user 10 is in the "permissible range" (step S149). If it is determined to be "good" (YES in step S149), the control unit 210 makes the intervention method to be an intervention method with low effectiveness (step S151).

If it assessed to be not "good" (NO in step S149), the control unit 210 assesses whether the progression is "fair", i.e., whether the current value of the index of the user 10 is in the "limit range" (step S150). If it is determined to be "fair" (YES in step S150), the control unit 210 makes the intervention method to be an intervention method with high effectiveness (step S152).

After step S151 and step S152, the control unit 210 assesses whether it is intervention timing (step S154). If it is assessed that it is intervention timing (YES in step S154), the control unit 210 executes processing for intervention (step S155). Thereafter, the control unit 210 returns the executing process to the call source of the process.

In the case of the intervention method with a low effectiveness being an intervention by a standard message transmitted to the user 10 from the server 200 via the information communication terminal 100, the intervention method with a high effectiveness is an intervention via a non-standard message sent from an associate of the user 10 or a professional (for example, a physician, a trainer, or the like) upon a request from the server 200.

In the case of the intervention method with a low effectiveness being an intervention by a message sent from a person of equal or lower status to the user 10 (for example, a family member (partner, child, parent, brother or sister) depending on a family composition or a friend) upon a request from the server 200, the intervention method with a high effectiveness is an intervention by a message sent from a person of higher status than the user 10 (for example, a company supervisor, a senior colleague, a teacher) upon a request from the server 200.

For each type of method of reaching the target, such as diet and exercise, the user 10 and an intervention person with a higher contribution toward the method of reaching the target is determined. Contribution refers to a grade classification (e.g., large, medium, small) of the size of the contribution. Environmental information such as the family composition and workplace environment of the user 10 and past practice data of the user 10 or other users is used in the determination.

For example, intervention results of the user 10 for each intervention person per type of target index are stored in the storage unit 220. Alternatively, intervention results of each of a plurality of persons per each intervention person are stored per type of target index in the storage unit 220. For intervention results, in the case where the value of the target index after intervention is improved, the intervention is stored as a success, and in the case where the value of the target index after intervention is not improved, the intervention is stored as a failure. Then, using the intervention result stored in the storage unit 220, the contribution is specified according to the number of successful interventions according to the target index, and an intervention person with a high contribution is determined.

The timing of intervention may be a time predetermined for each type of method of reaching the target. Also, execution timing information of the method of reaching the target may be obtained from the user 10 via the information communication terminal 100A, estimate, and determine the timing of intervention to be before or after the execution timing corresponding to the contents of the intervention.

The intervention results per each timing relating to a target are collected in the storage unit 220, and the collected intervention results may be used to determine a timing with high contribution.

For example, intervention results of the user 10 for each intervention timing per type of target index are stored in the storage unit 220. Alternatively, intervention results of a plurality of persons for each intervention timing per type of target index are stored in the storage unit 220. For intervention results, in the case where the value of the target index after intervention is improved, the intervention is stored as a success, and in the case where the value of the target index after intervention is not improved, the intervention is stored as a failure. Then, using the intervention result stored in the storage unit 220, the contribution is specified according to the number of successful interventions according to the target index, and an intervention timing with a high contribution is determined.

In the case where the lifestyle of the user 10 changes on weekdays, holidays and the like, even if the method of reaching the target and the contents of intervention are the same, the person who executes the intervention, and the intervention timing are preferably determined according to the change of lifestyle.

For example, in the case of the intervention content being "diet", when it is a weekday on working day of the user 10, just before lunch timing, a supervisor at work, i.e., a person of a higher status than the user 10, may be notified by the server 200 for target management to talk to the user 10 about the choice of lunch menu, prompting for performing an intervention for the user 10 about "diet".

In the case of the intervention content being "diet", when it is a holiday of not working day for the user 10, before the wife, i.e., the partner of the user 10, determine a lunch, the wife may be notified about lunch cooking method by the server 200 for target management, prompting for performing an intervention for the user 10 about "diet".

In the case of the intervention content being "exercise", when it is a weekday on working day of the user 10, before going to and leaving work, the user 10 may be notified by the server 200 for target management via the information communication terminal 100A of the user 10 to plan "exercise" such as walk fast, use the stairs, thus executing an intervention about "exercise".

In the case of the intervention content being "exercise", when it is a holiday of not working day for the user 10, before the holiday, the children of the user 10 may be notified of information about exercise that can be done on holidays by the server 200 for target management, thus prompting for performing an intervention for the user 10, who is a father, about "exercise".

Intervention by an intervention method with a high success rate (phone call from wife, in the case of methods listed from highest success rate being phone call from wife, a word from daughter, and notification via smart phone) from among methods of reaching the target of a plurality of persons with the same method of reaching the target as the user 10 can be considered to execute. For example, the server 200 for target management prompts the wife of the user 10 to perform intervention about "walking", which is the method of reaching the target, making the wife call the user 10 and tell a message such that "You have nearly reached your target, so why don't you walk from the station today?".

An intervention method that was effective in intervention for persons with the same characteristics as the user 10 may be used. For example, for a male in his 40 s, in the case of the methods listed from most effective being comment from daughter, designation of cooking method to wife, and notification to user via smart phone, the following is considered.

For days assessed to have a "fair" progression, the server 200 for target management prompting for intervention for the user 10 by notifying the daughter of the user 10 of the current state of the user 10 and requesting her to comment "How have you been doing?" is considered. In the case of an intervention about "diet", when the daughter talks to the father from 18:00 to 19:00, then prompting for intervention for the user 10 by the daughter at 18:30 during talking is considered.

For days assessed to have a "fair" progression, the server 200 for target management prompting for intervention about "diet" for the user 10 by notifying the wife of the user 10 of the current state of the user 10 and presenting an effective recipe is considered. If the wife thinks about what to cook at 13:00, then prompting for intervention for the user 10 by the wife about "diet" at just before then at 12:30 is considered.

On the day after the day when progression was assessed to be "fair", the server 200 for target management intervening by contacting the smart phone of the user to check on the current state is considered. If the user 10 takes meals at 6:00, 12:15, and 19:30, then intervention for the user 10 just before these times that are at 5:45, 12:00, and 19:15 is considered.

Returning to FIG. 15, if it is assessed that the progression is not "fair" (NO in step S150), the control unit 210 resets the target (step S156) and executes target realization second processing (step S157). A target reset may include changing the index target according to the current progression or extending the time limit for reaching the target. Thereafter, the control unit 210 returns the executing process to the call source of the process.

Effects of Embodiment

According to the embodiment described above, the effects described below can be obtained.

(1-1) In the target management system, the control unit 210 of the server 200 for target management calculates the degree of divergence of the current value of a predetermined index from a route corresponding to a transition in value of a predetermined index to a target value of a predetermined index for reaching a target relating to the body of the user 10, as indicated by step S141 to step S147 in FIG. 15. As indicated by step S148 to step S152, the control unit 210 determines an intervention method according to the calculated degree of divergence. As indicated by step S155, the control unit 210 executes processing for intervention for the user 10 by the determined intervention method. This can effectively prompt the user 10 to improve to reach a target relating to the body.

(1-2) As indicated by step S151 and step S152 of FIG. 15, the control unit 210 determines a person intervening for the user 10 as an intervention method. As indicated by step S155, the control unit 210 executes processing for prompting the person determined for intervention as processing for intervention for the user 10. In this manner, the user 10 can be effectively prompted by the determined intervention person to improve to reach a target relating to the body.

(1-3) As illustrated in FIG. 16 and FIG. 20, the storage unit 220 stores in advance determining information for determining a statistically effective intervention method. As indicated by step S151 and step S152 of FIG. 15, the control unit 210 determines a statistically effective intervention method for the user 10 using the determining information stored in the storage unit. In this manner, the user 10 can be effectively prompted by a statistically effective intervention method for the user 10 to improve to reach a target relating to the body.

(1-4) As illustrated in FIG. 20, the storage unit 220 associates and stores in advance the targets relating to a body of a plurality of persons and their effective intervention method as determining information. As indicated by step S151 and step S152 of FIG. 15, the control unit 210 determines an intervention method on the basis of the intervention methods for persons with similar targets to the user 10 from among the intervention methods stored in the storage unit 220. In this manner, the user 10 can be effectively prompted by a statistically effective intervention method for the user 10, specifically, intervention method for persons with similar targets to the user 10, to improve to reach a target relating to the body.

(1-5) As illustrated in FIG. 16, the storage unit 220 stores in advance an intervention method that was previously effective for the user as determining information. As indicated by step S151 and step S152 of FIG. 15, the control unit 210 determines an intervention method on the basis of the intervention methods stored in the storage unit 220. In this manner, the user 10 can be effectively prompted by a statistically effective intervention method for the user 10, specifically, an intervention method that was effective for the user 10 among previous intervention methods, to improve to reach a target relating to the body.

(2-1) In the target management system, the control unit 210 of the server 200 for target management assesses whether intervention is necessary due to an occurrence of a divergence of the current value of a predetermined index from a route corresponding to a transition in value of a predetermined index to a target value of a predetermined index for reaching a target relating to the body of the user 10, as indicated by step S141 to step S147 in FIG. 15. The storage unit 220 stores the results of intervention per each of persons that intervenes relating to the target index. As indicated by step S151 and step S152, when the control unit 210 determines, when assessed that intervention is necessary, a person with high contribution toward reaching the target from among the persons intervening for the user 10, using the intervention result stored in the storage unit 220. As indicated by step S155, the control unit 210 executes processing for prompting the person determined for intervention. This can effectively prompt the user 10 to improve to reach a target relating to the body. Also, the user 10 can be effectively prompted by the intervention person with high contribution toward reaching the target determined on the basis of the intervention results to improve to reach a target relating to the body.

(2-2) The storage unit 220 stores the results of intervention per each timing relating to the target. As indicated by step S154 of FIG. 15, the control unit 210 determines a timing with a high contribution toward reaching the target using the results of intervention stored in the storage unit 220. The execution unit executes processing for prompting the person intervening for intervention at the timing determined by the determination unit. This can effectively prompt the user 10 at a timing with a high contribution toward reaching the target to improve to reach a target relating to the body.

(2-3) As indicated by step S154 of FIG. 15, the control unit 210 determines a person with a high contribution corresponding to habits of the user 10 for each day. This can effectively prompt the user 10 by a person with a high contribution corresponding to a habit of the user 10 for each day to improve to reach a target relating to the body.

Modified Example (1) In the embodiments described above, the disclosure related to a target management system. However, no such limitation is intended, and the disclosure can be embodied as the server 200 and the information communication terminal 100 for target management included in a target management system. The disclosure can only be embodied as a program executed by the server 200 and the information communication terminal 100 and a method for target management.

The invention can also be embodied as a computer-readable recording medium in which the program is recorded. The recording medium may be a magnetic disc, such as a magnetic tape, a flexible disk, or a hard disk, an optical disk, such as a CD-ROM, a CD-R, a CD-RW, a DVD-ROM, a DVD-R, a DVD-RW, a DVD-RAM, a DVD+R, or a DVD+RW, a magneto-optical disk such as a MO, a memory card or a medium that stationarily carries a program such as USB memory, or a medium that fluidly carries a program in a manner that allows the program to be downloaded via a communication network from a server such as an application service provider (ASP).

(2) In the embodiments described above, the server 200 for target management is a single computer. However, no such limitation is intended, and the server 200 may be a server group configured by including a plurality of computers.

(3) In the embodiments described above, the functions executed by the target management system are achieved by software being executed by the CPU of the control unit 210, i.e., process of the program described referring to FIG. 14 and FIG. 15. However, no such limitation is intended, and one or more or all of these functions may be achieved by dedicated hardware.

(4) In the embodiments described above, one or more of the functions executed by the server 200 may be executed by the information communication terminal 100. For example, in the case where the control unit 210 of the server 200 specifies a predetermined value using predetermined data stored in the storage unit 220 and sends the specified predetermined value to the information communication terminal 100, the control unit 210 of the server 200 may send the predetermined data stored in the storage unit 220 to the information communication terminal 100 and specify a predetermined value using predetermined data received by the control unit 110 of the information communication terminal 100.

(5) The technology described in the embodiments and modified examples are intended to be applied individually and in combination as far as possible.

The embodiments described herein are illustrative in all respects and are not intended as limitations. The scope of the present disclosure is indicated not by the descriptions of the embodiments described above but by the claims and includes all meaning equivalent to the scope and changes within the scope.

REFERENCE SIGNS LIST

10, 20, 30 User
100, 100A, 100B, 100C Information communication terminal
110, 210, 510 Control unit
120, 220, 520 Storage unit
130, 530 Operation unit
140, 540 Output unit
150, 250 External storage device
151, 251 Recording medium
160, 170, 570 Wireless communication unit
200, 300 Server
260 Communication unit
500 Measuring device
580 Measurement unit
800, 800A, 800B Communication facility
900 Communication Network

The invention claimed is:

1. A target management system, comprising:
an assessment unit configured to assess whether intervention is necessary due to an occurrence of a divergence of a current value of a predetermined index from a route corresponding to a transition in value of the predetermined index to a target value of the predetermined index for reaching a target relating to a body of a user;

a storage unit configured to store an intervention result per each of persons intervening relating to a target index;

a determination unit configured to determine, when the assessment unit assesses that intervention is necessary, a person with a high contribution toward reaching the target, from among the persons intervening for the user, using the intervention result stored in the storage unit; and an execution unit configured to execute processing for prompting a person determined by the determination unit for intervention.

2. The target management system according to claim 1, wherein the storage unit is configured to further store an intervention result per each timing of intervention relating to a target index;

the determination unit is configured to determine a timing with a high contribution toward reaching the target using an intervention result stored in the storage unit; and the execution unit is configured to execute processing for prompting the person intervening for intervention to intervene at the timing determined by the determination unit.

3. The target management system according to claim 1, wherein the determination unit is configured to determine a person with high contribution corresponding to a habit of the user for each day.

4. The target management system according to claim 1, further comprising:

a calculation unit configured to calculate a degree of divergence of the current value of the predetermined index from the route, wherein the determination unit is configured to determine an intervention method corresponding to the degree of divergence, and the execution unit is configured to execute processing for intervention for the user by the intervention method.

5. The target management system according to claim 4, wherein the determination unit is configured to determine a person intervening for the user as the intervention method; and the execution unit is configured to execute processing for prompting the person determined by the determination unit for intervention as processing for intervention for the user.

6. The target management system according to claim 4, further comprising:

a storage unit configured to store in advance determining information for determining a statistically effective intervention method, wherein the determination unit is configured to determine a statistically effective intervention method for the user using the determining information stored in the storage unit.

7. The target management system according to claim 6, wherein the storage unit is configured to associate and store in advance a target relating to a body of each of a plurality of persons and an effective intervention method as the determining information, and the determination unit is configured to determine an intervention method on the basis of an intervention method for a person with a similar target to the user from among the intervention methods stored in the storage unit.

8. The target management system according to claim 6, wherein the storage unit is configured to store in advance an intervention method that was previously effective for the user as the determining information, and the determination unit is configured to determine an intervention method on the basis of the intervention method stored in the storage unit.

9. A non-transitory recording medium comprising a target management program executed by a server including a storage unit configured to store an intervention result per each of persons intervening relating to a target index relating to a body of a user, the target management program comprising the steps executed by the server of: assessing whether intervention is necessary due to an occurrence of a divergence of a current value of a predetermined index from a route corresponding to a transition in value of the predetermined index to a target value of the predetermined index for reaching a target relating to a body of a user; determining, when assessed that intervention is necessary, a person with a high contribution toward reaching the target, from among the persons intervening for the user, using the intervention result stored in the storage unit; and executing processing for prompting a person determined for intervention.

10. The non-transitory recording medium comprising the target management program according to claim 9, further comprising the steps executed by the server of: calculating a degree of divergence of the current value of the predetermined index from the route; determining an intervention method corresponding to the degree of divergence calculated; and executing processing for intervention for the user by the intervention method determined.

* * * * *